| United States Patent [19]
Godtfredsen et al.

[11] Patent Number: 4,831,025
[45] Date of Patent: May 16, 1989

[54] CRYSTALLINE PENICILLIN DERIVATIVE TOSYLATE HYDRATES

[75] Inventors: Wagn O. Godtfredsen, Værlose; Welf von Daehne, Rungsted Kyst, both of Denmark

[73] Assignee: Leo Pharmaceutical Products Ltd., Ballerup, Denmark

[21] Appl. No.: 24,858

[22] Filed: Mar. 13, 1987

Related U.S. Application Data

[63] Continuation of Ser. No. 314,021, Oct. 22, 1981, abandoned.

[30] Foreign Application Priority Data

Oct. 31, 1980 [GB] United Kingdom ................ 8035156

[51] Int. Cl.$^4$ ..................... A61K 31/43; C07D 499/32
[52] U.S. Cl. ..................... 514/195; 540/315; 540/336
[58] Field of Search ................ 540/315, 336; 514/195

[56] References Cited

U.S. PATENT DOCUMENTS 4,244,951  1/1981  Bigham ................ 514/195

FOREIGN PATENT DOCUMENTS 881675  8/1980  Belgium .

Primary Examiner—Paul J. Killos
Assistant Examiner—Vera C. Clarke
Attorney, Agent, or Firm—Cushman, Darby & Cushman

[57] ABSTRACT

The present invention relates to a crystalline hydrate of a salt of the antimicrobial agent 1,1-dioxopenicillanoyloxymethyl 6-(D-α-amino-α-phenylacetamido)-penicillanate with p-toluenesulfonic acid, more particularly the mono- and dihydrate.

The hydrates are easily obtained in a crystalline state devoid of organic solvent residues, they show good stability on storage, they are effectively absorbed and hydrolyzed in vivo, and they are thus specifically suitable for medical treatment of patients, in particular for oral administration.

23 Claims, 2 Drawing Sheets

CRYSTALLINE PENICILLIN DERIVATIVE TOSYLATE HYDRATES

This is a continuation of application Ser. No. 314,021, filed Oct. 22, 1981, which was abandoned upon the filing hereof.

The present invention relates to the pure, crystalline salt of the antimicrobial agent 1,1-dioxopenicillanoyloxymethyl 6-(D-α-amino-α-phenylacetamido)penicillanate with p-toluenesulfonic acid.

More particularly, the invention relates to crystalline hydrated forms of this salt, to pharmaceutical compositions containing these, to dosage units of such compositions, to methods for treating patients (including animals) with the above salt and compositions (including compounded composition), and to methods for the preparation of the salt and compositions.

Specifically, the invention relates to the mono- and dihydrate of 1,1-dioxopenicillanoyloxymethyl 6-(D-α-amino-α-phenylacetamido)penicillanate tosylate.

"Mono- and dihydrate" indicates, here and in the following, salts, the production of which is reproducible and leads to products with a water content conforming with a mono- or a dihydrate.

The two drawing figures relate to the IR-spectrums of the crystalline hydrates in KBr and details are given in Examples 1 and 2 herein.

For easy reference 1,1-dioxopenicillanoyloxymethyl 6-(D-α-amino-α-phenylacetamido)penicillanate and its tosylate are hereinafter also designated VD 1827 and VD 1827 tosylate, respectively.

The preparation, the properties and the use of VD 1827 are disclosed in the Specification to British patent application No. 8,002,682.

VD 1827 is an orally active antibiotic intended for the treatment of infectious diseases. VD 1827 and many of its salts are readily absorbed upon oral administration, and during or after absorption hydrolyzed with liberation of ampicillin and the β-lactamase inhibitor penicillanic acid 1,1-dioxide in equimolar amounts, giving rise to high blood and tissue concentrations of the two components concomitantly.

VD 1827 can be prepared e.g. by reacting chloromethyl 6-(D-α-azido-α-phenylacetamido)penicillanate with potassium penicillanate 1,1-dioxide in a first step and in a second step the azido group of the reaction product is hydrogenated to form the desired VD 1827.

Other methods are available, e.g. methods in which iodomethyl penicillanate 1,1-dioxide is reacted with a salt of ampicillin with a temporarily protected amino group in which method the last step comprises removing the protecting group, e.g. by acid hydrolysis.

Certain salts of VD 1827, such as the hydrochloride, have a tendency to form solvates with organic solvents which may be disadvantageous, among other things from a stability point of view. Certain other salts may be difficult to obtain in a crystalline state.

In addition, easily soluble salts, such as the hydrochloride of VD 1827, may give rise to certain formulation problems.

With VD 1827 tosylate these difficulties have been overcome. VD 1827 tosylate is sparingly soluble in water and is easily obtained in the crystalline state devoid of organic solvent residues.

It has been found to show good stability on storage, and to be well suited for the preparation of various pharmaceutical forms of presentation.

A slightly soluble salt of VD 1827 is known, namely its napsylate. The tosylate of VD 1827 is, however, somewhat more soluble than the napsylate and is being absorbed faster than the latter, whereby higher peak serum concentrations are achieved. The VD 1827 tosylate is therefore especially suited for treatment of systemic infections where high blood and tissue concentrations are of importance.

The efficient absorption and in vivo hydrolysis of VD 1827 tosylate dihydrate and the corresponding monohydrate are illustrated in Tables I and II, respectively. The Tables show serum concentrations and urinary recoveries of ampicillin and penicillanic acid 1,1-dioxide after oral administration of the drug to healthy volunteers.

TABLE I

Serum Concentrations (mcg per ml) and Urinary Excretion (in percent of dose administered) of Ampicillin (A) and Penicillanic Acid 1,1-Dioxide (B) in Fasting Volunteers following Oral Administration of 492 mg VD 1827 tosylate dihydrate, corresponding to 214 mg anhydrous Ampicillin and 143 mg Penicillanic Acid 1,1-Dioxide in Aqueous Suspension.

| | Serum concentrations | | | | | | | | | | | |
|---|---|---|---|---|---|---|---|---|---|---|---|---|
| | Hours after administration | | | | | | | | | | | |
| | ½ | | 1 | | 2 | | 3 | | 4 | | 6 | |
| Subject | A | B | A | B | A | B | A | B | A | B | A | B |
| DR | 6.9 | 7.7 | 7.5 | 4.7 | 2.6 | 2.3 | 1.3 | 0.83 | 0.72 | 0.34 | 0.23 | 0.21 |
| IB | 5.4 | 5.6 | 5.2 | 5.1 | 1.7 | 1.8 | 0.71 | 1.2 | 0.33 | 0.47 | 0.10 | 0.47 |
| AS | 7.6 | 14.0 | 4.3 | 4.2 | 1.5 | 1.8 | 0.65 | 0.46 | 0.31 | 0.24 | 0.08 | <0.04 |
| CH | 4.7 | 7.3 | 5.2 | 5.9 | 1.7 | 1.2 | 0.63 | 0.21 | 0.26 | 0.16 | 0.11 | 0.05 |
| HD | 6.7 | 11.1 | 4.0 | 3.6 | 1.2 | 0.79 | 0.46 | 0.06 | 0.21 | 0.06 | 0.07 | 0.06 |
| LA | 7.2 | 8.6 | 5.0 | 3.8 | 2.3 | 1.5 | 1.1 | 0.60 | 0.58 | 0.58 | 0.24 | 0.13 |
| Mean | 6.4 | 9.1 | 5.2 | 4.6 | 1.8 | 1.6 | 0.81 | 0.56 | 0.40 | 0.31 | 0.14 | 0.18 |

| | Urinary excretion | | | | | | | | | |
|---|---|---|---|---|---|---|---|---|---|---|
| | Hours after administration | | | | | | | | | |
| | 0–3 | | 3–6 | | 6–12 | | 12–24 | | 0–24 | |
| Subject | A | B | A | B | A | B | A | B | A | B |
| DR | 55.5 | 52.8 | 5.3 | 7.4 | 2.2 | 3.8 | 0.27 | 0.2 | 63.3 | 64.1 |
| IB | 64.4 | 68.1 | 5.9 | 8.0 | 1.3 | 1.6 | 0.09 | 0.1 | 71.7 | 77.8 |
| AS | 55.9 | 57.8 | 22.2 | 23.7 | 2.0 | 4.4 | 0.23 | 3.5 | 80.3 | 89.5 |
| CH | 58.8 | 49.6 | 6.0 | 6.1 | 2.7 | 3.7 | 0.37 | 0.7 | 67.9 | 60.1 |
| HD | 56.8 | 40.2 | 8.8 | 12.2 | 0.88 | 2.0 | 0.12 | 0.6 | 66.6 | 55.0 |
| LA | 58.1 | 50.2 | 6.0 | 7.4 | 0.99 | 2.3 | 0.13 | 0.1 | 65.2 | 60.0 |

TABLE I-continued

Serum Concentrations (mcg per ml) and Urinary Excretion (in percent of dose administered) of Ampicillin (A) and Penicillanic Acid 1,1-Dioxide (B) in Fasting Volunteers following Oral Administration of 492 mg VD 1827 tosylate dihydrate, corresponding to 214 mg anhydrous Ampicillin and 143 mg Penicillanic Acid 1,1-Dioxide in Aqueous Suspension.

| Mean | 58.3 | 53.1 | 9.0 | 10.8 | 1.7 | 3.0 | 0.20 | 0.9 | 69.2 | 67.8 |
|---|---|---|---|---|---|---|---|---|---|---|

TABLE II

Serum Concentrations (mcg per ml) and Urinary Excretions (in percent of dose administered) of Ampicillin (A) and Penicillanic Acid Sulfone (B) in Volunteers Following Oral Administration of two Tablets VD 1827 tosylate monohydrate corresponding to 490 mg VD 1827 free base (288 mg ampicillin and 192 mg penicillanic acid sulfone) immediately after a light breakfast*

| | Serum Concentrations Hours after Administration | | | | | | | | | | | | |
|---|---|---|---|---|---|---|---|---|---|---|---|---|---|
| | 1/4 | | 3/4 | | 1 | | 1½ | | 2 | | 4 | | 6 | |
| Subject | A | B | A | B | A | B | A | B | A | B | A | B | A | B |
| BN | 5.7 | 5.6 | 7.9 | 5.1 | 5.0 | 3.8 | 3.7 | 2.6 | 4.4 | 3.1 | 1.1 | 0.9 | 0.26 | 0.2 |
| EN | 5.9 | 5.5 | 14.0 | 16.1 | 12.3 | 12.0 | 9.0 | 10.1 | 5.2 | 5.8 | 1.7 | 0.7 | 0.57 | 0.2 |
| HP | 6.4 | 3.1 | 9.4 | 8.4 | 10.1 | 6.6 | 6.7 | 4.5 | 3.7 | 4.3 | 0.96 | 0.1 | 0.27 | <0.1 |
| OB | 10.1 | 5.6 | 9.8 | 5.4 | 6.6 | 4.8 | 3.9 | 3.3 | 2.6 | 9.7 | 0.57 | 3.3 | 0.17 | <0.1 |
| AS | 12.2 | 9.2 | 9.1 | 6.3 | 6.2 | 3.9 | 3.5 | 3.1 | 2.1 | 1.2 | 0.45 | 0.5 | 0.11 | <0.2 |
| HD | 4.9 | 4.0 | 7.1 | 7.4 | 5.9 | 6.0 | 3.7 | 3.0 | 2.3 | 2.3 | 0.40 | — | 0.11 | <0.2 |
| SH | 3.3 | 3.6 | 8.4 | 7.2 | 6.6 | 3.7 | 5.0 | 2.4 | 3.7 | 2.2 | 0.87 | 0.7 | 0.28 | 1.1 |
| LA | 14.7 | 13.0 | 9.8 | 9.7 | 7.2 | 5.6 | 5.0 | 4.5 | 3.2 | 2.1 | 0.81 | 1.0 | 0.29 | <0.2 |
| Mean | 7.9 | 6.2 | 9.4 | 8.2 | 7.5 | 5.8 | 5.1 | 4.2 | 3.4 | 3.8 | 0.86 | 1.0 | 0.26 | <0.3 |

| | Urinary Excretion Hours after Administration | | | | | | | | | |
|---|---|---|---|---|---|---|---|---|---|---|
| | 0–3 | | 3–6 | | 6–12 | | 12–24 | | 0–24 | |
| Subject | A | B | A | B | A | B | A | B | A | B |
| BN | 54.0 | 59.7 | 14.6 | 18.7 | 1.9 | 2.6 | 0.03 | 0.7 | 70.5 | 82 |
| EN | 53.8 | 67.0 | 14.6 | 16.4 | 2.1 | 2.8 | 0.49 | 3.9 | 71.0 | 90 |
| HP | 66.1 | 54.3 | 15.3 | 27.5 | 3.0 | 4.5 | 0.06 | <0.1 | 84.5 | 86 |
| OB | 58.2 | 74.9 | 7.1 | 11.4 | 1.4 | 3.2 | 0.18 | 0.9 | 66.9 | 90 |
| AS | 38.7 | 60.5 | 21.9 | 30.9 | 0.96 | 1.4 | 0.33 | <0.5 | 61.9 | 93 |
| HD | 56.1 | 62.4 | 10.9 | 16.8 | 1.5 | 2.0 | 0.05 | <1 | 68.6 | 82 |
| SH | 52.4 | 54.3 | 17.5 | 17.7 | 3.6 | 4.8 | 0.37 | <1 | 73.9 | 77 |
| LA | 45.4 | 39.3 | 28.8 | 33.3 | 2.1 | 4.0 | 0.56 | <1 | 76.9 | 77 |
| Mean | 53.1 | 59.1 | 16.3 | 21.6 | 2.1 | 3.2 | 0.26 | <1 | 71.8 | 84 |

*A roll with butter and a cup of coffee

VD 1827 is, as well as p-toluenesulfonic acid, a non-toxic compound, and thus the salt according to the invention is suitable for medical treatment of patients.

Due to their physico-chemical properties, the hydrated forms of VD 1827 tosylate have also proved appropriate with a view to a commercial scale manufacture.

The present compounds can be prepared by known methods for salt formation. In one embodiment they are prepared by reacting the free p-toluenesulfonic acid with VD 1827 in a suitable medium with a view of accomplishing the desired reaction.

In another embodiment the present compounds can be prepared in a single or double decomposition, e.g. by reacting the hydrochloride of VD 1827 with the free p-toluene-sulfonic acid or its salts, e.g. with alkali metals or organic bases.

Thus, in some embodiments, the pertinent conditions are that protonized VD 1827 is brought together with p-toluene-sulfonate ions in a suitable medium with a view to obtaining the VD 1827 tosylate directly as a precipitate, or indirectly by in a first step removing the by-product of the reaction, e.g. potassium chloride, and in a second step recovering the desired salt by evaporation of the solvent and crystallization. Alternatively it may be precipitated by adding a solvent in which its solubility is low. The expert can easily select the appropriate solvent or mixture of solvents having knowledge of the solubility of VD 1827 tosylate and the solubilities of the starting substances used and the by-products formed in the process.

In a specific embodiment of the invention, the formation of VD 1827 tosylate is obtained by adding p-toluenesulfonic acid when removing the amino protecting group in the last step in the synthesis of VD 1827, whereby VD 1827 is readily recovered as its tosylate (cf. Example 3), which can be recrystallized to form the pure salt.

In another embodiment, amorphous VD 1827 tosylate is crystallized from an organic solvent or a mixture of solvents, at least containing the appropriate amount of water.

Due to their low solubilities in water, the hydrates of VD 1827 tosylate will in many instances crystallize directly from aqueous solutions. Thus, e.g. the dihydrate may be obtained in this manner.

Other crystalline hydrated forms of VD 1827 tosylate may be obtained by various methods.

VD 1827 tosylate dihydrate may be dried in vacuo at 50° C. to give VD 1827 tosylate monohydrate (cf. Example 4).

The dihydrate may be recrystallized from an organic solvent or a mixture of organic solvents to give a product containing less water, e.g. recrystallization from methanol/isopropanol gives the monohydrate (cf. Example 2).

The solubilities of the present compounds are as follows:

Very slightly soluble: isopropanol, ethyl acetate, ether, hexane;
Slightly soluble: acetone, ethanol; water;
Soluble: dimethylformamide, methanol, dimethylsulfoxide, acetonitrile;
At 25° C., the solubilities in water of VD 1827 tosylate hydrates are approx. 0.5%.

The crystallization and recrystallization are usually undertaken at temperatures between −30° C. and 80° C., preferably between −10° C. and 30° C.

Details of the various embodiments will appear from the examples.

It is a further object of the invention to provide pharmaceutical compositions, including compounded compositions, which are useful in the treatment of infectious diseases in the human and veterinary practice, and which may be used for enteral, parenteral or topical administration, but preferably for enteral use.

In the following (except the Examples) the designation VD 1827 tosylate is used, irrespective of its water content.

With this object in view, the compositions of the invention contain as an active component at least VD 1827 tosylate together with solid or liquid pharmaceutical carriers and/or diluents.

In the said compositions, the proportion of therapeutically active material to carrier substance can vary between 1% and 95% by weight. The compositions can be worked up to various pharmaceutical forms of presentation, such as disintegrating and effervescent tablets, pills, dragees, suppositories, capsules, powders, suspensions, intramammaries, ointments, and the like.

Pharmaceutically acceptable, non-toxic, organic or inorganic, solid, semisolid or liquid carriers and/or auxiliary agents can be used to make up compositions containing the present compounds. Gelatine, sugars and sugar alcohols, starches, starch derivatives, cellulose and cellulose derivatives, magnesium or calcium stearate, talc, naturally occurring or modified, vegetable and animal fats and oils, mineral oils, gums, polyalkylene glycols, polyvinyl derivatives, buffers, organic acids, carbonates, or other known carriers and/or auxiliary agents for medicaments are all suitable.

Furthermore, the compositions may contain other therapeutically active components which can appropriately be administered together with the VD 1827 tosylate in the treatment of infectious diseases, such as other antibacterials, antiviral agents, antifungal drugs, antitussives, pain-relieving drugs, probenecid, etc. In particular, antibacterials, which act synergistically with one or both of the active components formed by in vivo hydrolysis of the VD 1827 tosylate, are appropriate. Such compounded compositions may be administered in mixtures or in forms where the active components are separated from each other, e.g. in multi-layer tablets or core tablets.

As indicated above, the present compositions may be worked up to any pharmaceutical forms of presentation for human or veterinary use.

For enteral administration, it is usually preferred to provide compositions which ensure a fast absorption from the gastro-intestinal tract. Instead of using disintegrating tablets, an effervescent tablet, or a suspension containing VD 1827 tosylate may be used. A capsule dissolving in the gastric juice and containing a powder with a content of VD 1827 tosylate may also be used.

However, compositions giving rise to a sustained release of the active components may also be used in certain cases.

Another object of the invention resides in the selection of a dose of the VD 1827 tosylate and a dosage unit of the compositions of the invention which dose and dosage unit can be administered so that the desired activity is achieved without simultaneous secondary effects. In the human therapy the present compounds are conveniently administered (to adults) in dosage units of the compositions containing not less than 50 mg and up to 2500 mg, preferably from 100 mg to 1000 mg calculated as the VD 1827 tosylate.

By the term "dosage unit" is meant a unitary, i.e. a single dose which is capable of being administered to a patient, and which may be readily handled and packed, remaining as a physically stable unit dose comprising either the active material as such or a mixture of it with solid or liquid pharmaceutical diluents, carriers, solvents and/or auxiliary agents.

In the form of a dosage unit, the VD 1827 tosylate may be administered once or more times a day at appropriate intervals, always depending, however, on the condition of the patient, and in accordance with the prescription made by the medical practitioner.

Thus a daily dose in adult patients will typically be an amount of from 0.25 to 15 g, preferably from 0.5 g to 5 g, of VD 1827 tosylate, which conveniently can be divided into several single doses.

In the continuous therapy of patients suffering from infectious diseases, the disintegrating or effervescent tablets, capsules, or suspensions are the appropriate forms of pharmaceutical preparations. In some instances, as mentioned above, sustained-release formulations may be used as well.

In the veterinary practice the above pharmaceutical compositions may also be used, preferably in the form of dosage units containing from 50 mg up to 25 g of VD 1827 tosylate.

For the treatment of mammary disorders, especially bovine mastitis, the antibacterial agent can be administered by the intramammary route in liquid or semiliquid form, such as an ointment, or together with a substantially water-insoluble and oil-insoluble binding agent in the form of granules. In compounded mastitis formulations, penethamate, or its hydriodide, is an appropriate component.

Still another object of the invention is to provide a method of treating patients suffering from infectious diseases, the method comprising administering to adult patients an effective amount of VD-1827 tosylate, preferably in the form of the dosage units aforesaid. The VD 1827 tosylate is typically administered in amounts of 3–200 mg/kg body weight of the patient/day, preferably in amounts from 7 to 70 mg/kg body weight of the patient/day, corresponding to, for adult human patients, from 0.25 g to 15 g per day, preferably from 0.5 g to 5 g per day.

In the treatment of patients, the present compounds can be administered either alone or together with other therapeutically active compounds, e.g. as the compounded compositions mentioned above. Such combined treatment can be performed with formulations containing more or all of the therapeutically active compounds, or these may be administered in separate formulations, these being given simultaneously or with suitable intervals.

In the treatment of patients, the daily dose is administered either at one time, or in divided dosages, e.g. two, three or four times a day.

The invention will be further described in the following Examples which are not to be construed as limiting the invention.

EXAMPLE 1

VD 1827 tosylate dihydrate

VD 1827 hydrochloride (6.3 g, 10 mmole) was dissolved in a mixture of water (40 ml) and acetone (10 ml). A solution of sodium 4-toluenesulfonate (1.94 g, 10 mmole in water (10 ml) was added dropwise with stirring. After stirring for 1 hour at room temperature and 2 hours at 5° C., the crystalline precipitate was collected, washed with water (2×10 ml) and dried in vacuo to yield the title compound as colourless crystals with melting point 141°-148° C. dec.

Water content (K.F. method): 5.1%.

Figure 1:
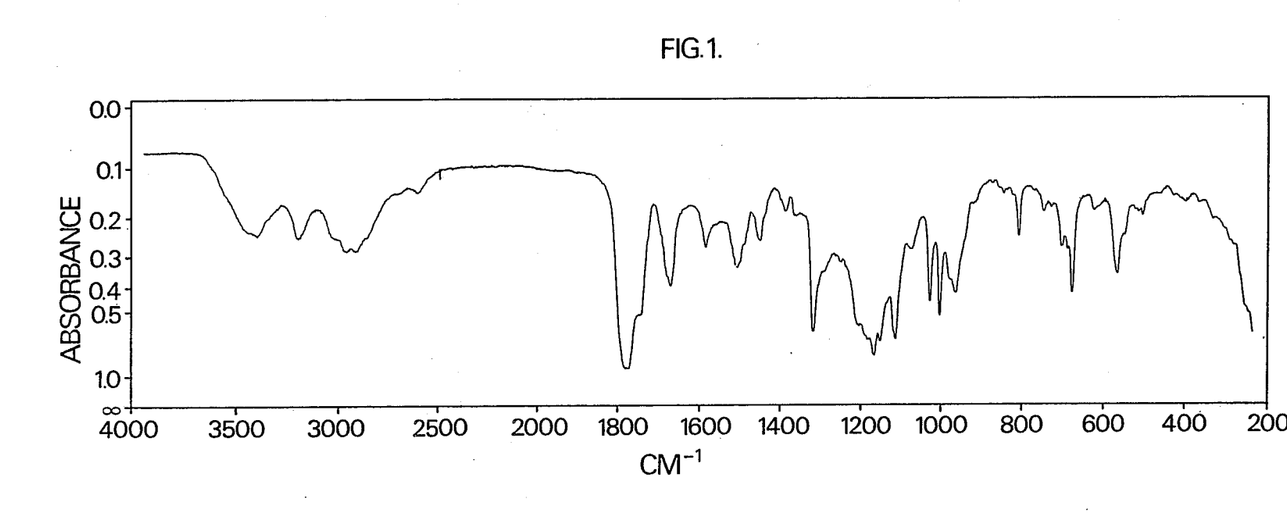

The IR-spectrum (KBr) showed strong bands at: 1790, 1680, 1515, and 1325 cm$^{-1}$. (cf. FIG. 1).

The NMR-spectrum [(CD$_3$)$_2$SO] showed signals at $\delta = 1.37$ (s, 6H), 1.48 (s, 6H), 2.32 (s, 3H), 3.1-3.8 (m, 2H), 4.47 (s, 1H), 4.57 (s, 1H), 5.2 (m, 2H), 5.6 (m, 2H), 5.95 (s, 2H), 7.15 (d, J=7.5, 2H), 7.5 (m, 7H), 8.7 (bs, 3H), 9.45 (d, J=6, 1H) ppm. Tetramethylsilane was used as internal reference.

EXAMPLE 2

VD 1827 tosylate monohydrate

The compound described in Example 1 (10 g) was dissolved in methanol (40 ml) at 40° C. Seeding crystals were added, and the mixture was slowly cooled to room temperature. After standing at 5° C. overnight, isopropanol (80 ml) was added dropwise, and the mixture was stirred, for 2 hours at 5° C. The precipitate was filtered off, washed with hexane (20 ml) and air-dried.

Melting point: 151°-53° C. (dec.)

Found: C: 48.90, H: 5.23, N: 7,12, H$_2$O: 2.70%. C$_{32}$H$_{38}$N$_4$O$_{12}$S$_3$, H$_2$O requires: C: 48.97, H: 5.14, N: 7.14, H$_2$O: 2.29%

$[\alpha]_D^{20} = +185°$ (c=1, ethanol)

Figure 2:
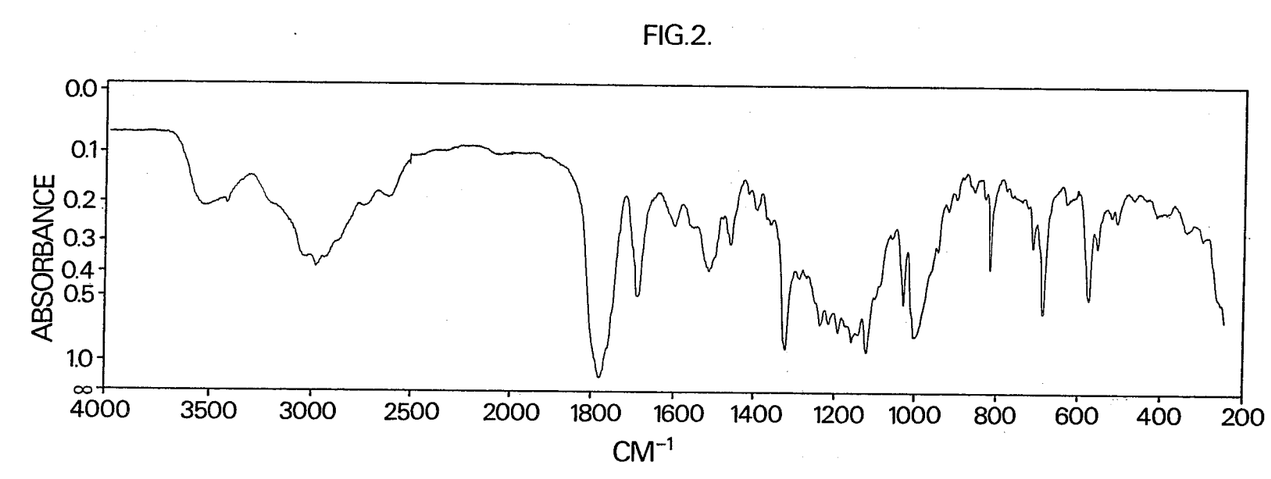

The IR-spectrum (KBr) showed strong bands at 1780, 1685, 1510, 1410, and 1320 cm$^{-1}$ (cf. FIG. 2).

When subjected to Debye Scherrer X ray diffraction (Gunier camera) using CrK$_{\alpha I}$ radiation ($\lambda = 2.28962$ Å), the above product exhibited d-values (d) and line intensities (I) as summarized in the Table III. Line intensities were determined visually and characterized as follows: st=strong, m=medium, w=weak.

TABLE III

| d(Å) | I | d(Å) | I | d(Å) | I | d(Å) | I |
|---|---|---|---|---|---|---|---|
| 14.9 | w+ | 6.99 | m | 4.70 | w+ | 3.55 | w− |
| 14.3 | st | 6.90 | w− | 4.66 | w+ | 3.44 | w |
| 13.7 | m− | 6.72 | w | 4.61 | w | 3.13 | w |
| 10.8 | w | 6.62 | m | 4.59 | w | 2.98 | w+ |
| 10.5 | w | 6.59 | w− | 4.56 | w | 2.88 | w− |
| 9.96 | w | 6.38 | w+ | 4.43 | w− | 2.83 | w− |
| 9.53 | m | 5.88 | m+ | 4.01 | st− | 2.69 | w− |
| 8.78 | w− | 5.57 | st | 3.77 | w+ | 2.58 | w |
| 7.67 | w+ | 5.34 | w+ | 3.76 | w− | 2.38 | w |
| 7.50 | w | 5.29 | m− | 3.65 | w | 2.33 | w? |
| 7.28 | w | 5.16 | w | 3.59 | w | 2.27 | w− |
| 7.17 | w | 4.79 | w+ | 3.56 | w− | 2.22 | w− |
|  |  |  |  |  |  | 2.09 | w− |

EXAMPLE 3

Preparation of VD 1827 and its tosylate

To a suspension of potassium carbonate (1.66 g, 12 mmole) in dimethylformamide (25 ml), were added methyl acetoacetate (2.38 ml, 22 mmole) and anhydrous ampicillin (3.84 g, 11 mmole). The mixture was stirred for 3 hours at room temperature, followed by 18 hours at 5° C. Iodomethyl penicillanate 1,1-dioxide (3.73 g, 10 mmole) was added, and stirring was continued for 20 minutes at 5°-10° C. After dilution with ethyl acetate (100 ml), the mixture was extracted with water (4×25 ml) and saturated aqueous sodium chloride (25 ml) to give a solution of the intermediate, 6$\beta$-[N-(1-methoxycarbonyl-propen-2-yl)-D-$\alpha$-amino-$\alpha$-phenylacetamido]penicillanoyloxymethyl penicillanate 1,1-dioxide, in ethyl acetate. The intermediate was hydrolyzed at an apparent pH-value of 1 (glass-calomel combination electrode) by dropwise addition of a solution of 4-toluenesulfonic acid monohydrate (1.90 g, 10 mmole) in ethyl acetate (20 ml). After addition of about 5 ml of the solution, the mixture was seeded, and a crystalline precipitate was formed. The mixture was stirred for 2 hours at 5° C., whereafter the crystals were filtered off, washed with ethyl acetate (2×10 ml), and air-dried.

The dried product was dissolved in methanol (40 ml) at 40° C. Water (80 ml) was added, and crystallization was induced by scratching and cooling in an ice-bath. After stirring for 1 hour at 5° C., the crystals were filtered off, washed with water (2×10 ml), and dried in vacuo to give a product identical to that described in Example 1.

EXAMPLE 4

VD 1827 tosylate monohydrate

The compound described in Example 1 was dried in vacuo for 18 hours at 50° C. to give the title compound as colourless crystals m.p. 151°-53° C.

Found: C: 49.08, H: 5.38, N: 7.05, H$_2$O: 2.29% C$_{32}$H$_{38}$N$_4$O$_{12}$S$_3$, H$_2$O requires: C: 48.97, H: 5.14, N: 7.14, H$_2$O: 2.29%.

EXAMPLE 5

VD 1827 tosylate dihydrate

To an ice-cooled solution of potassium 6-[N-(1-methoxycarbonylpropen-2-yl)-D-$\alpha$-amino-$\alpha$-phenylacetamido]penicillanate (415.5 g) in dimethyl formamide (750 ml), iodomethyl penicillanate 1,1-dioxide (279.1 g) was added with stirring. After stirring for 40 minutes at approximately 5° C., ethyl acetate (2 liter) was added and the resulting solution washed with water (400 ml), followed by saturated aqueous sodium chloride (400 ml). The washings were extracted with ethyl acetate (2×400 ml), whereupon the ethyl acetate phases were combined and washed with saturated aqueous sodium chloride (2×400 ml) to give a solution containing the amino-protected VD 1827. This was hydrolyzed at an apparent pH-value of 2.5-3 (glass calomel electrode) by addition of a solution of 4-toluenesulfonic acid monohydrate (142.5 g) in ethyl acetate (1 liter). After stirring for 1 hour at 5° C., the crystals were filtered off, washed with ethyl acetate and dried to give 550.9 g of the crude title compound.

Recrystallization; method A:

350 g of the above crude VD 1827 tosylate dihydrate was dissolved in methanol (1 liter) at 40° C., and water (1 liter) was added with stirring. The mixture was seeded, and, after stirring and ice-cooling for two hours, additional water (1 liter) was added. The crystals were collected, washed with water (500 ml), slurried in isopropanol (1.5 liter) to remove excess water, filtered off, and washed with hexane (1 liter). Air drying afforded 286 g of pure VD 1827 tosylate dihydrate.

Found: C: 47.51, H: 5.38, N: 6.92%.

$C_{32}H_{38}N_4O_{12}S_3$, 2 $H_2O$ requires: C: 47.87, H: 5.27, N: 6.98%.

The above product was subjected to Debye Scherrer X ray diffraction (Gunier camera) using $CrK_{60\ I}$ radiation ($\lambda = 2.28962$ Å) to exhibit the d-values (d) and line intensities (I) summarized in Table IV below. Line intensities were determined visually (st=strong, m=medium, w=weak).

TABLE IV

| d(Å) | I | d(Å) | I | d(Å) | I | d(Å) | I |
|---|---|---|---|---|---|---|---|
| 19.9 | m— | 6.14 | w | 4.83 | w | 3.78 | w— |
| 14.6 | m | 5.91 | m— | 4.68 | w | 3.73 | w— |
| 10.4 | w? | 5.77 | m | 4.55 | w— | 3.44 | w |
| 8.52 | w— | 5.54 | m— | 4.03 | w— | 3.32 | w— |
| 7.93 | w+ | 5.22 | w | 3.93 | w+ | 3.23 | w— |
| 6.81 | w+ | 4.99 | m+ | 3.85 | w | 2.59 | w, diffuse |
| | | | | | | 2.42 | w |

Recrystallization; method B:

200 g of crude VD 1827 tosylate dihydrate was dissolved in methanol (800 ml) at 40° C., and seeding crystals were added. Isopropanol (1.5 l) was slowly added with stirring. The crystals were filtered off, washed with hexane (500 ml), and air-dried to afford 169.6 g of pure VD 1827 tosylate dihydrate.

Found: C: 48.04, H: 5.41, N: 6.96, $H_2O$: 4.41%. $C_{32}H_{38}N_4O_{12}S_3$, $2H_2O$ requires: C: 47.87, H: 5.27, N: 6.98, $H_2O$: 4.48%.

EXAMPLE 6

To a suspension of VD 1827 free base (2.97 g, 5 mmole) in dry ethyl acetate (50 ml), a solution of anhydrous 4-toluenesulfonic acid (0.86 g, 5 mmole) in dry ethyl acetate (25 ml) was added dropwise with stirring. A clear solution was formed, which was evaporated in vacuo to yield the anhydrous VD 1827 tosylate as a white solid.

The anhydrous product was dissolved in methanol (20 ml) at 40° C. Water (40 ml) was added, and crystallization was induced by scratching and cooling in an ice-bath. After stirring for 1 hour at 5° C., the crystals were filtered off, washed with water (2×5 ml), and dried in vacuo to give a product identical to that described in Example 1.

EXAMPLE 7

| Powder for aqueous suspension | |
|---|---|
| Component | Per 100 ml of suspension |
| VD 1827 tosylate dihydrate | 5.00 g |
| Tween 20 | 0.05 g |
| Sucrose | 40.00 g |
| Sodium citrate | 0.60 g |
| Sodium caragheenate | 0.40 g |

| -continued | |
|---|---|
| Powder for aqueous suspension | |
| Component | Per 100 ml of suspension |
| Flavour (q.s.) | |
| | 46.05 g |

The active compound is micronized, the other ingredients are added, and the mixture is carefully blended to obtain a uniform product. From the resulting powder an aqueous suspension is prepared by addition of purified water to a total volume of 100 ml.

EXAMPLE 8

| Tablets | |
|---|---|
| Component | |
| VD 1827 tosylate dihydrate | 5000 g |
| Corn starch | 750 g |
| Methyl cellulose | 50 g |
| Carboxymethyl starch | 250 g |
| Magnesium stearate | 50 g |
| | 6100 g |

The active compound is blended with the corn starch and granulated with a 5% solution of methyl cellulose in deionized water. After drying at 50° C. and screening through 0.75 mm screens, the granules are blended with carboxymethyl starch and magnesium stearate. The resulting mixture is compressed into tablets each weighing 610 mg.

EXAMPLE 9

| Capsules | |
|---|---|
| Component | Per capsule |
| VD 1827 tosylate dihydrate | 250 mg |
| Lactose | 50 mg |
| Methyl cellulose | 2.5 mg |
| Magnesium stearate | 2.5 mg |
| | 305 mg |

The active ingredient and the lactose are granulated with a 5% solution of methyl cellulose in de-ionized water, dried at 50° C., and screened through 1 mm sieves. To the granules is added magnesium stearate, the mixture is carefully blended, and 305 mg of the blend are filled into No. 2 gelatine capsules.

EXAMPLE 10

| Veterinary suspension | |
|---|---|
| VD 1827 tosylate dihydrate | 100 g |
| 12-Hydroxystearin* | 20 g |
| Coconut oil modified** | 880 g |
| | 1000 g |

*Trademark "THIXIN ®"
**Tradmark "NEOBEE ®"

12-Hydroxystearin is dissolved in coconut oil at 70° C. and cooled to room temperature. VD 1827 tosylate dihydrate is incorporated by agitation followed by homogenization. The suspension is filled into plastic syringes each containing 5 g of the suspension.

EXAMPLE 11

| Veterinary suspension | |
|---|---|
| Penethamate hydriodide | 20 g |
| VD 1827 tosylate, dihydrate | 40 g |
| Framycetin sulfate | 20 g |
| Aluminium monostearate | 20 g |
| 12-Hydroxystearin | 10 g |
| Liquid paraffin | 890 g |
| | 1000 g |

Aluminum monostearate and 12-hydroxystearin are dissolved in liquid paraffin at 130° C. and cooled to 30° C. Penethamate hydriodide, VD 1827 tosylate dihydrate and framycetin sulfate are incorporated by agitation followed by homogenization. The suspension is filled into plastic syringes each containing 5 g of the suspension.

EXAMPLE 12

| Effervescent tablet | |
|---|---|
| Components | |
| VD 1827 tosylate monohydrate | 250 mg |
| Citric acid | 600 mg |
| Sodium hydrogencarbonate | 400 mg |
| Polyethylenglycol 6000 | 20 mg |
| Sodium saccharine | 20 mg |

The powders are premixed, sieved and mixed again. The mixed powders are compressed to tablets.
Tablet weight: 1.290 grams
Punch size: circular, diameter 18 mm, plane surface.

EXAMPLE 13

| Tablets | |
|---|---|
| Components | |
| VD 1827 tosylate monohydrate | 5000 g |
| Corn starch | 750 g |
| Methyl cellulose | 50 g |
| Sodium carboxymethyl starch | 250 g |
| Magnesium stearate | 50 g |
| | 6100 g |

The active compound is blended with the corn starch and granulated with a 5% solution of methyl cellulose in deionized water. After drying at 50° C. and screening through 0.75 mm screens, the granules are blended with sodium carboxymethyl starch and magnesium stearate. The resulting mixture is compressed into tablets each weighing 610 mg.

EXAMPLE 14

| Capsule 250 mg | |
|---|---|
| Components | |
| VD 1827 tosylate monohydrate | 2500 g |
| Poly(vinylpolypyrrolidone)* | 250 g |
| Magnesium stearate | 25 g |
| | 2775 g |

*Plasdone XL ®, GAF

The components are mixed, sieved through a 0.7 mm sieve and filled into gelatine capsules each containing 277.5 mg of the powder mixture.

EXAMPLE 15

| Powder for aqueous suspension | |
|---|---|
| Components | |
| VD 1827 tosylate dihydrate | 2500 g |
| Sucrose | 30000 g |
| Sodium citrate | 250 g |
| Sodim carboxymethylcellulose | 250 g |
| Flavour | q.s. |

*Plasdone XL ®, GAF

The components are sieved through a sieve 0.5 mm, mixed and filled into unit dose sachets each containing 3.3 g of powder, equivalent to 250 mg of VD 1827 tosylate dihydrate.

EXAMPLE 16

| Suppository 400 mg | |
|---|---|
| Components | |
| VD 1827 tosylate monohydrate | 4000 g |
| Hard fat* | 21000 g |

*e.g. Witepsol W 25 ®, Dynamit Nobel

The VD 1827 tosylate monohydrate is sieved through a sieve 0.125 mm and suspended into the melted hard fat not exceeding 40° C. The mixture is dosed into suppository moulds using a suitable suppository machine. Each suppository weighes 2.5 g, equivalent to a content of 400 mg of VD 1827 tosylate monohydrate.

EXAMPLE 17

| Intramammary | |
|---|---|
| Components | |
| VD 1827 tosylate monohydrate | 100 g |
| 12-Hydroxystearin* | 20 g |
| Coconut oil modified** | 880 g |
| | 1000 g |

*Trademark "THIXIN ®"
**Trademark "NEOBEE ®"

12-Hydroxystearin is dissolved in coconut oil at 70° C. and cooled to room temperature. VD 1827 tosylate monohydrate is incorporated by agitation followed by homogenization. The suspension is filled into plastic syringes each containing 5 g of the suspension.

EXAMPLE 18

| Multilayer tablet | |
|---|---|
| Each tablet contains | |
| VD 1827 tosylate monohydrate | 250 mg |
| VD 1825* hydrochloride | 250 mg |
| Components for granulate A | |
| VD 1827 tosylate monohydrate | 2500 g |
| Corn starch | 375 g |
| Methylcellulose | 25 g |
| Sodium carboxymethyl starch | 125 g |
| Magnesium stearate | 25 g |
| | 3050 g |

*VD 1825 is 1,1-dioxopenicillanoyloxymethyl 6-[(hexahydro-1H—azepin-1-yl)-methyleneamino]penicillanate.

Granulate A is manufactured as indicated in example 13.

| Components for granulate B | |
|---|---|
| VD 1825* hydrochloride | 2500 g |
| Lactose | 520 g |
| Magnesium stearate | 30 g |
| | 3050 g |

The components are mixed, compressed into a slugging machine. The slugs are crushed and sieved to a granule size of approximately 1 mm.

The two granulates A and B are compressed to multilayer tablets, each layer weighing 305 mg.

EXAMPLE 19

| Pediatric tablet | |
|---|---|
| Components | |
| VD 1827 tosylate monohydrate | 2500 g |
| Corn starch | 375 g |
| Methylcellulose | 25 g |
| Sodium carboxymethyl starch | 125 g |
| Magnesium stearate | 25 g |
| | 3050 g |

The tablets are manufactured as described in example 13, each tablet weighing 305 mg and containing 250 mg VD 1827 tosylate monohydrate.

EXAMPLE 20

| Coated granulate | |
|---|---|
| Components | |
| VD 1827 tosylate dihydrate | 5000 g |
| Corn starch | 500 g |
| Methylcellulose | 100 g |
| Hydroxypropylmethylcellulose | 500 g |
| Sucrose | 20000 g |
| Sodium carboxymethylcellulose | 500 g |
| | 26600 g |

VD 1827 tosylate dihydrate and corn starch are mixed and wet granulated with methylcellulose dissolved in an appropriate amount of water. The dried granulate is slugged and broken down to granules. Granules of sizes 0.5–0.8 mm are collected by sieving. Too coarse or too fine granules are reprocessed. The granules are coated in a fluid-bed process with an aqueous solution of hydroxypropylmethyl cellulose. The coated granules are mixed with sucrose and sodium carboxymethylcellulose and filled in sachets, each containing 2.66 grams and containing 500 mg VD 1827 tosylate dihydrate.

EXAMPLE 21

| Tablet | |
|---|---|
| Components for granulate A | |
| VD 1827 tosylate monohydrate | 2000 g |
| Corn starch | 300 g |
| Methylcellulose | 20 g |
| Sodium carboxymethyl starch | 100 g |
| Magnesium stearate | 20 g |
| | 2440 g |

Granulate A is manufactured as indicated in example 13.

| Components for granulate B | |
|---|---|
| Pivmecillinam hydrochloride | 2000 g |
| Lactose | 420 g |
| Magnesium stearate | 20 g |
| | 2440 g |

The compounds are mixed, compressed into a slugging tablet machine. The slugs are crushed and sieved to a granule size of approximately 1 mm.

The two granulates A and B are compressed into two-layer tablets, each layer weighing 244 mg. Each tablet contains 200 mg VD 1827 tosylate monohydrate and 200 mg pivmecillinam hydrochloride.

EXAMPLE 22

| Tablet | |
|---|---|
| Components | |
| VD 1827 tosylate monohydrate | 2500 g |
| Pivampicillin | 1250 g |
| Povidone* | 250 g |
| Microcrystalline cellulose | 2000 g |
| Magnesium stearate | 60 g |
| | 6060 g |

*Povidone = 1-vinyl-2-pyrrolidinone polymers

The components are sieved through a sieve 0.7 mm, mixed and compressed using a slugging tablet machine. The slugs are crushed and sieved to a granule size of approximately 1 mm.

The granulate are compressed to tablets each weighing 606 mg. Each tablet contains 250 mg VD 1827 tosylate monohydrate and 125 mg pivampicillin.

What we claim is:

1. Crystalline 1,1-dioxopenicillanoyloxymethyl 6-(D-α-amino-α-phenylacetamido)penicillanate tosylate hydrates.

2. A compound according to claim 1, characterized in having a water content corresponding to a dihydrate.

3. A compound according to claim 1, characterized in having a water content corresponding to a monohydrate.

4. Method for producing a compound according to claim 1, characterized in that 1,1-dioxopenicillanoyloxymethyl 6-(D-α-amino-α-phenylacetamido)penicillanate or a salt thereof is reacted with p-toluenesulfonic acid or one of its salts in a suitable medium with a view to accomplishing the formation of the crystalline compound, which is recovered and optionally recrystallized in order to obtain a product with the desired water content.

5. Method for producing a compound of claim 1, characterized in that an amino-protected derivative of 1,1-dioxopenicillanoyloxymethyl 6-(D-α-amino-α-phenylacetamido)penicillanate is reacted with p-toluenesulfonic acid resulting in cleavage of the protecting group and formation of a compound of claim 1.

6. Method for producing a compound of claim 1, characterized in subjecting 1,1-dioxopenicillanoyloxymethyl 6-(D-α-amino-α-phenylacetamido)penicillanate tosylate to crystallization from a suitable solvent or a mixture of solvents containing a sufficient amount of water to accomplish formation of the desired crystalline hydrate.

7. An antimicrobial or antibacterial composition, comprising as an active ingredient an effective amount of a compound according to claim 1 together with a pharmaceutically acceptable, non-toxic carrier.

8. A composition according to claim 7 in dosage unit form for enteral, parenteral or topical administration to patients suffering from bacterial infections.

9. A composition according to claim 8 for oral treatment of patients, containing from 50 mg to 2500 mg of the active ingredient.

10. A composition according to claim 9, in which the active ingredient has a water content approximately corresponding to a dihydrate.

11. A composition according to claim 9, in which the active ingredient has a water content approximately corresponding to a monohydrate.

12. A composition according to claim 8 in the form of slow release tablets, effervescent tablets, pills, or capsules.

13. A composition according to claim 7 in form of a suspension.

14. A composition according to claim 7 in form of a powder.

15. A composition according to claim 7 in form of an intramammary preparation.

16. A composition according to claim 7 in form of an ointment.

17. A composition according to claim 8 in which the active ingredient constitutes from 1% to 95% of the composition.

18. A compounded composition according to claim 8 which contains one or more additional active compounds selected from the group consisting of $\beta$-lactam antibiotics, antiviral agents, antifungal drugs, antitussives, pain-relieving drugs and probenecid.

19. A composition according to claim 18 in form of a multilayer tablet or a core tablet.

20. A process for the treatment of patients suffering from microbial or bacterial diseases which comprises administering thereto an effective amount of a compound according to claim 1.

21. A treatment according to claim 20, comprising the administration of an amount of the active compound of 3–200 mg/kg body weight of the patient/day.

22. A treatment according to claim 21 of an adult human being, comprising a daily administration of from 0.5 g to 5 g of the active compound.

23. A process for the treatment of a patient suffering from a microbial or bacterial disease which comprises administering thereto one or more additional active compounds selected from the group consisting of -lactam antibiotics, antiviral agents, antifungal drugs, antitussives, pain-relieving drugs, and probenecid, the additional administration being undertaken simultaneously with the administration of a compound according to claim 1, or at spaced intervals with respect to the administration of said compound.

* * * * *